United States Patent [19]

Bardos et al.

[11] Patent Number: 4,886,790

[45] Date of Patent: Dec. 12, 1989

[54] NOVEL BIS(2,2-DIMETHYL-1-AZIRIDINYL) PHOSPHINIC AMIDES FOR USE IN THE TREATMENT OF TUMORS

[75] Inventors: Thomas J. Bardos, Snyder, N.Y.; Michael E. Perlman, Durham, N.C.; Joan E. MacDiarmid, Amherst, N.Y.

[73] Assignee: The Research Foundation of State University of New York, Albany, N.Y.

[21] Appl. No.: 163,283

[22] Filed: Mar. 2, 1988

Related U.S. Application Data

[60] Division of Ser. No. 779,147, Sep. 23, 1985, abandoned, which is a continuation-in-part of Ser. No. 484,213, Apr. 12, 1983, abandoned, which is a continuation-in-part of Ser. No. 367,338, Apr. 12, 1982, abandoned.

[51] Int. Cl.$^4$ .................. A61K 31/675; C07D 203/06
[52] U.S. Cl. ....................................... 514/83; 548/956
[58] Field of Search ........................................ 514/83

[56] References Cited

U.S. PATENT DOCUMENTS

| | | | |
|---|---|---|---|
| 2,606,900 | 8/1952 | Parker et al. | 260/239 |
| 2,663,705 | 7/1951 | Parker et al. | 260/247.5 |
| 2,670,347 | 2/1954 | Kuh et al. | 260/239 |
| 3,201,313 | 8/1965 | Bardos et al. | 167/78 |

FOREIGN PATENT DOCUMENTS

| | | |
|---|---|---|
| 1094046 | 11/1953 | France . |
| 313878 | 6/1956 | Switzerland . |
| 715861 | 9/1954 | United Kingdom . |
| 729586 | 5/1955 | United Kingdom . |
| 864021 | 3/1961 | United Kingdom . |
| 906428 | 9/1962 | United Kingdom . |

OTHER PUBLICATIONS

Heidelberger, et al., Chem. Abstracts, vol. 52 (1958), entry 4022 h-i.
Pujman, Chem. Abstracts, vol. 51 (1957), entry 2171 d-e.
Munson, et al., Cancer Chemotherapy Reports, vol. 51(5), (1967), pp. 253–259.
Wampler et al., Absence of Cross-Resistance to Alkylating Agents in Cyclophosphamide-Resistant L1210 Leukemia, Europ. J. Cancer, vol. 14, pp. 977–982, 1978.
Bardos et al., Synthesis of Potential Dual Antagonists III, Jour. of Pharmaceutical Sciences, vol. 54, No. 2, Feb., 1965.
Chmielewicz et al., Synthesis and Chemotherapeutic Effects of Ethyl Bis-(2,2-Dimethyl)-Ethylenamido Phosphate. A Preliminary Report, Jour. of Pharmaceutical Sciences, vol. 56, No. 9, Sep. 1967.
Wodinsky et al., Combined Therapy with an Aziridine Derivative NSC 200724 (AB182) and Radiation on an Experimental Leukemia. Int. J. Radiation Oncology Biol. Phys., vol. 5, pp. 1677–1680, 1979.
Hsiao et al., Synthesis of New Bis (1-Aziridinyl) Phosphinate Alkylating Agents Containing O-Phenyl N-- Phenylcarbamate Side Chains, Jour. of Med. Chem., vol. 16, p. 391, 1973.
Lalka et al., Reactions of 2,2-Dimethyl-Aziridine-Type Alkylating Agents in Biological Systems I: Colorimetric Estimation and Stability in Physiological Media, Jour. of Pharmaceutical Sciences, vol. 62, No. 8, Aug., 1973.
Bardos et al., Synthesis of Potential Dual Antagonists IV, Jour. of Pharmaceutical Sciences, vol. 54, No. 3, Mar., 1965.
Hsiao et al., Synthesis of Bis(Aziridinyl)Phosphinyl-N-Hydroxy-Urethane Derivatives as Antineoplastic Agents, Jour. of Medical Chemistry, vol. 18, p. 195, 1975.
Bardos et al., Combination of Chemotherapy with Dual Antagonists and Radiotherapy in the Treatment of Neoplastic Disease, Journal of Surgical Oncology 3(4); pp. 431–441, 1971.
Bardos et al., Structure–Activity Relationships of Alkylating Agents in Cancer Chemotherapy, Annals of the New York Academy of Sciences, vol. 163, Article 2, pp. 1006–1025, Oct. 3, 1969.
Chmielewicz et al., Alterations of Some Macromolecular and Bio Chemical Properties of Calf Thymus DNA Caused by "Dual Antagonists", and Nitrogen Mustard, Cancer Research, 27, pp. 1248–1257, Jul. 1967.
Munson et al., Preparation and Antitumor Activity of Tris (2,2-Dimethyl-1-Aziridinyl)Phosphine Oxide (Tepa-132), Cancer Chemotherapy Reports, vol. 51, No. 5, pp. 253–259, Sep. 1967.
Bardos et al., Effects of Ring-C-Methyl Substituents on the Chemical and Biological Activities of Ethylenimine Type Alkylating Agents, Int. Congress of Chemotherapy, Jun. 1967.
Bardos, Antimetabolites: Molecular Design and Mode of Action, Topics in Current Chemistry, vol. 52, pp. 90 and 92 only, 1974.

(List continued on next page.)

Primary Examiner—Mukund J. Shah
Assistant Examiner—C. L. Cseh

[57] ABSTRACT

A method of inhibiting the replication of tumor cells is disclosed wherein Novel bis (2,2-dimethyl-1-aziridinyl)-phosphinic amide antineoplastic agents of the formula:

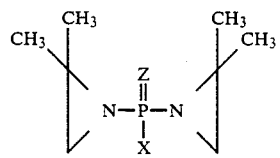

wherein X is

R and R' are each, independently, hydrogen, alkyl, substituted alkyl, phenyl and substituted phenyl, Y is alkyl or substituted alkyl of 1–10 carbon atoms and, Z is oxygen or sulfur is administered to tumor cells.

18 Claims, No Drawings

OTHER PUBLICATIONS

Lalka et al., Cyclophosphamide, 2,2-Dimethyl-Aziridines and Other Alkylating Agents as Inhibitors of Serum Cholinesterase, Biochemical Pharmacology, vol. 24, pp. 455–462, 1975.

Lalka et al., Reactions of 2,2-Dimethyl-Aziridine-Type Alkylating Agents in Biological Systems II: Comparative Pharmacokinetics in Dogs, Jour. of Pharmaceutical Sciences, vol. 64, No. 2, Feb., 1975.

Bardos et al., Chemical Mechanism of the Radiation Potentiating Effects of 2,2-Dimethylaziridine-Type Antitumor Agents, Int. J. Radiation Oncology Biol. Phys., vol. 5, pp. 1653–1656, 1979.

Wampler et al., Radiation Potentiating Effect of Ethyl Bis(2,2-Dimethyl-1-Aziridinyl)Phosphinate (AB–163), Int. J. Radiation Oncology Biol. Phys., vol. 5, pp. 1681–1683, 1979.

Hsiao et al., Synthesis of 5'-Thymidinyl Bis(1-Aziridinyl) Phosphinates as Antineoplastic Agents, Jour. of Med. Chemistry, vol. 24, pp. 887–889, 1981.

Zhdanov et al., Biologically Active Stable Radicals: XV[1] Spin-Labeled Alkyl Carbamate-N-Phosphonic Acid Aziridides, "Synthesis", pp. 269–271, 1979.

Koneiczny et al., Methods for the Preparation of Spin-Labeled Phosphorus Compounds and Applications of Some of them to Phosphorylative Spin-Labeling, "Synthesis", Sep. 1981.

Kimler et al., Development and Testing of New Hypoxic Cell Radiosensitizers, Radiology, vol. 33, pp. 515–157, 1979.

Heidelberger, C., "The Effect of Several Phosphoramides on Transplanted Tumors", *Cancer Research*, 17, 277–283 (1957).

Pujman, V., "Leukemia of Mice Strain C 57 Black", Roxpravy (MPV) Ceskoslov. Akad. Ved. 66, No. 10, 1–27 (1965).

NOVEL BIS(2,2-DIMETHYL-1-AZIRIDINYL) PHOSPHINIC AMIDES FOR USE IN THE TREATMENT OF TUMORS

This is a divisional of application Ser. No. 779,147, filed Sept. 23, 1985, which in turn is a continuation-in-part of U.S. Ser. No. 484,213, filed Apr. 12, 1983, which in turn is a continuation-in-part of U.S. Ser. No. 367,338, filed Apr. 12, 1982 all now abandoned.

TECHNICAL FIELD

This invention relates to phosphoraziridine amide compositions and to their use as antineoplastic agents. The invention more particularly relates to novel phosphoraziridine amide compositions having use in controlling replication of tumor cells. The compositions also find utility as antibacterials and certain of the compositions may find utility as other pesticides such as fungicides, nematocides and other antimicrobials.

BACKGROUND ART

Cancer is a general term used when referring to any disease state that results from an abnormal uncontrolled and progressive cellular growth. There are presently three principal methods available for the treatment of cancer. These methods are surgery, radiotheraphy and chemotheraphy. Typically, though surgery and radiotherapy may be effective by themselves, chemotherapy is usually administered in combination therewith to assure favorable results. A common example of such a combination would be the utilization of surgery to remove a tumor followed by treatment with certain chemicals capable of controlling or eliminating remaining cells which may move through the body to seed the growth of additional tumor sites (metastasis). Thus, typically a heavy reliance is placed on chemotherapy regardless of the treatment selected.

Unfortunately, such treatment with chemicals continues to have very serious disadvantages. In particular, none of the approximately 30 drugs commonly used in cancer chemotherapy have proven to be capable of totally eliminating the cancer disease except in a relatively small number of cases. Furthermore, most of the commonly used chemicals have very high general toxicity to the animal or can cause serious side effects relative to the dosage required to be effective against the abnormal cellular replication (neoplasm). The use of prior art chemicals in chemotherapy, therefore, very often results in serious complications which endanger the human being or other host organism being treated. These disadvantages of cancer treating chemicals (antineoplstic drugs) continue despite the fact that many thousands of potential antineoplastic agents have been screened and tested.

Many of the effective antineoplastic agents are classified as alkylating agents, i.e. a substance which introduces an alkyl, or substituted alkyl radical into a compound in place of a hydrogen atom. In chemicals utilized for treating cancer such alkylation frequently occurs within a nucleic acid structure such as DNA or RNA of the cancer cell thus effectively preventing the cell from functioning or reproducing.

A number of such alkylating agents contain one or more aziridine rings or contain intermediate structures which can yield aziridine rings. An aziridine ring is a three-membered heterocyclic ring containing one nitrogen atom and two carbon atoms. Examples of alkylating chemicals which contain aziridine rings or contain structures which can yield aziridine rings are as follows:

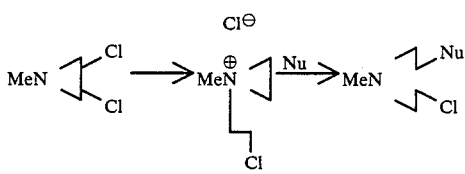

Mechanism of Nitrogen Mustard Alkylation

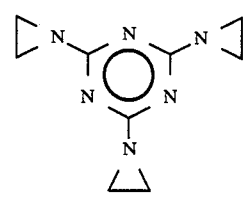

TEM

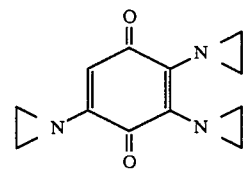

Treninon

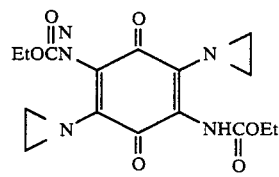

AZO

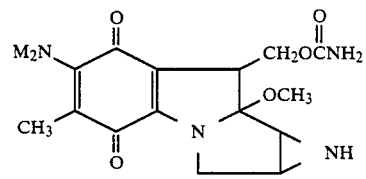

Mitomycin C

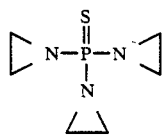

ThioTEPA

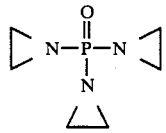

TEPA

-continued

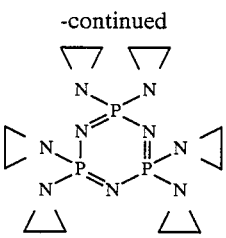

Apholate

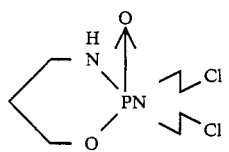

Cyclophosphamide

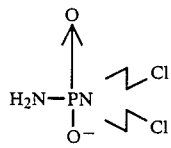

Phosphoramide Mustard

These compounds are believed to open at the aziridine ring site, if they are not already open, and then combine with a biological target molecule usually a nucleic acid, or, to be susceptible to nucleophilic displacement of the nitrogen from an aziridine ring carbon by a biological target nucleophile, such as a nucleoside base, to interrupt the replication of the nucleic acid or to interfere with messages which would be transmitted by the nucleic acid.

In addition to the thio-TEPA and TEPA compounds, numerous other phosphoraziridines are known. Phosphoaziridines are described in numerous publications, for example, in U.S. Pat. No. 2,606,900 to Parker et al; U.S. Pat. No. 3,201,313; to Bardos et al; in the Journal of Surgical Oncology 3(4) at pp 431–441 (1971) by Bardos et al; by Kimler et al in Radiology, 133 at pp 515–517 (1979); by Bardos et al in the International Journal of Radiation Oncology Biological Physics, Volume 5 at pp 1653–1656 (1979); by Wampler et al in International Journal of Radiation Oncology Biological Physics, Volume 5 at pp 1681–1683 (1979); and by Chmielewicz et al in the Journal of Pharmaceutical Sciences, Volume 56, No. 9 at pp 1179–1181 (1967).

Initially, phosphoraziridines were considered and classified as alkylating agents. In some cases, the diaziridinyl phosphinoyl group was chemically combined through an amide linkage to ethyl carbamate in an attempt to obtain a synergistic effect between the phosphoraziridine and urethane group. Such compounds derived from unsubstituted aziridines demonstrate potent anti-tumor activity but showed no significant clinical advantage over other alkylating agents.

Bis(2,2-dimethyl-1-aziridinyl) phosphinates were subsequently developed which showed the interesting characteristic of not only being chemicals suitable for chemotherapy but demonstrated the ability to potentiate the therapeutic effects of radiation upon transplanted tumors. The Bis(2,2-dimethyl-1-aziridinyl) phosphinates which were connected with urethane groups or ester groups nevertheles show highly effective anti-tumor cell activity with remarkably low toxicity for inhibiting the production and development of blood cells (hematopoietic toxicity) when compared with conventional alkylating agents.

BRIEF DESCRIPTION OF THE INVENTION

In accordance with the invention, there is provided a method for inhibiting the growth of tumor cells by the direct effects of chemotherapy. In accordance with the method, compounds of the invention are used as a chemotherapeutic agent and tumor cells are exposed to an effective cell replicaton inhibiting concentration of a compound of the invention.

The compounds useful in the method of the invention comprise two aziridine rings and have the formula:

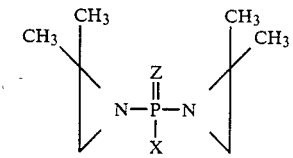

wherein X is selected from the group consisting of

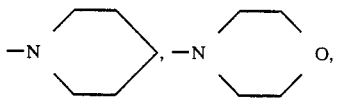

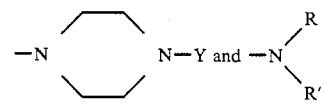

wherein R and R' are independently hydrogen, alkyl of 1–6 carbon atoms, substituted alkyl of 1–10 carbon atoms, phenyl or substituted phenyl, Y is alkyl or substituted alkyl of 1–10 carbon atoms, and, Z is oxygen or sulfur.

Novel compounds of the invention comprise those having the formula:

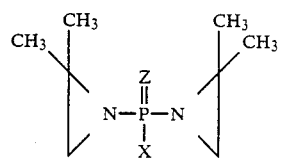

wherein X is selected from the group consisting of

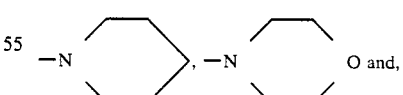

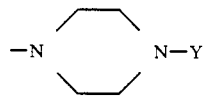

wherein Y is alkyl or substituted alkyl of 1–10 carbon atoms, and Z is oxygen or sulfur.

Representative alkyl groups encompassed within the description of Y, R and R' include substituted and unsubstituted, branched, straight chain and cyclic methyl, ethyl, propyl, butyl, pentyl, cyclopentyl, hexyl, and the like, up to about 10 carbon atoms. Representative substituents for the substituted alkyl include halogen such as chlorine, iodine, fluorine and bromine, hydroxy, amine, nitro, alkoxy, phenyl, sulfonate, substituted phenyl and the like. Repreventative substituents for the substituted phenyl include: halogen such as chlorine, fluorine, bromine and iodine, hydroxy, nitro, alkoxy, amine, sulfonate and the like.

Typical compounds encompassed within the description of the invention include: P,P-bis(2,2-dimethyl-1-aziridinyl)-phosphinic amide; P,P-bis(2,2-dimethyl-1-aziridinyl)thiophosphinic amide; P,P-bis(2,2-dimethyl-1-aziridinyl)-N-methylphosphinic amide; P,P-bis(2,2-dimethyl-1-aziridinyl)-N,N-dimethylphosphinic amide; P,P-bis(2,2-dimethyl-1-aziridinyl)-N-(methyl)-thiophosphinic amide; P,P-bis(2,2-dimethyl-1-aziridinyl)-N,N-(dimethyl)thiophosphinic amide; P,P-bis(2,2-dimethyl-1-aziridinyl)-N-ethylphosphinic amide; P,P-bis(2,2-dimethyl-1-aziridinyl)-N-(ethyl)thiophosphinic amide; P,P-bis(2,2-dimethyl-1-aziridinyl)-N-propylphosphinic amide; P,P-bis(2,2-dimethyl-1-aziridinyl)-N-(propyl)thiophinic amide; P,P-bis(2,2-dimethyl-1-aziridinyl)-N-butylphosphinic amide; P,P-bis(2,2-dimethyl-1-aziridinyl)-N-(butyl)thiophosphinic amide; P,P-bis(2,2-dimethyl-1-aziridinyl)-N-(3-methoxy-1-propyl)phosphinic amide; P,P-bis-(2,2-dimethyl-1-aziridinyl)-N-(3-(dimethylamino)-1-propyl)phosphinic amide; P,P-bis(2,2-dimethyl-1-aziridinyl)-N-phenylphosphinic amide; P,P-bis(2,2-dimethyl-1-aziridinyl)-N-(5-diethylamino-1-pentyl)phosphinic amide; P,P-bis(2,2-dimethyl-1-aziridinyl)-N-(5-diethylamino)-2-pentyl)-phosphinic amide; P,P-bis-(2,2-dimethyl-1-aziridinyl)-N-cyclohexylphosphinic amide; P,P-bis(2,2-dimethyl-1-aziridinyl)-N-(3'-methoxy-4'-nitrophenyl)phosphinic amide; P,P-bis(2,2-dimethyl-1-aziridinyl)-N-(p-chlorophenyl)phosphinic amide; P,P-bis(2,2-dimethyl-1-aziridinyl)-N-(p-fluorophenyl)phosphinic amide; P,P-bis(2,2-dimethyl-1-aziridinyl)-N-(p-dimethylaminophenyl)phosphinic amide; P,P-bis(2,2-dimethyl-1-aziridinyl)-N-(8-hydroxy-1-octyl)phosphinic amide; P,P-bis(2,2-dimethyl-1-aziridinyl)-N-benzylphosphinic amide, P,P-bis(2,2-dimethyl-1-aziridinyl)phosphinic piperidide; P,P-bis(2,2-dimethyl-1-aziridinyl)phosphinic morpholide; P,P-bis(2,2-dimethyl-1-aziridinyl)phosphinic-N'-methyl piperazide and the like.

The compounds of the invention can generally be prepared by the reaction of a 1:2 mole ratio of an appropriate phosphorus oxy or thio halide, such as phosphoryl chloride or phosphorus oxy bromide, with 2,2-dimethyl-1-aziridine in accord with the formula:

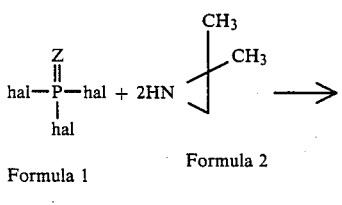

Formula 1    Formula 2

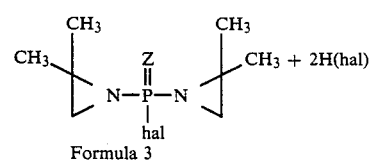

Formula 3

The resulting bis(2,2-dimethyl-1-aziridinyl)phosphinic or thiophosphinic halide is therefore reacted with an appropriate amine, morpholine or piperidine in the presence of an inert solvent to produce the final phosphinic amide in accordance with the formula:

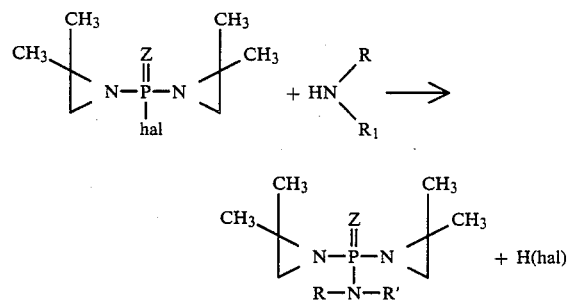

In general, the compounds of formula 3 prepared by the reaction of compounds of formula 2 with PO (hal)$_3$ or PS(Hal)$_3$ in the presence of an appropriate halogen acceptor are achieved by the methods described in U.S. Pat. No. 3,201,313 to Bardos et al; by U.S. Pat. No. 2,606,900 to Parker et al; and, in the previously described article by Chmielewicz et al which appeared in the Journal of Pharmaceutical Science, Volume 56, No. 9, Sept. 1967 at pages 1179–1181. The reactions are generally carried out in an inert atmosphere to avoid the presence of moisture, at temperatures from about 0° to about −50° C.

The 2,2-dimethyl-1-aziridine of formula 2 can be prepared by methods of the prior art for example by Wenker and Gabriel synthesis. The Wenker synthesis is described in the Journal of the American Chemical Society, Volume 57 at 2328 (1935) and the Gabriel synthesis is described in Ber. Volume 21 at page 1049 (1881).

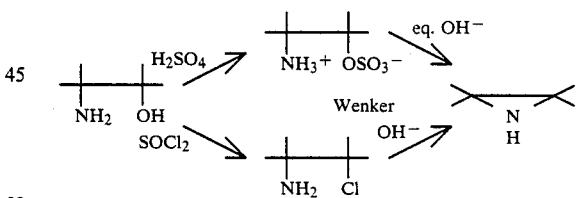

Other methods for preparation of intermediates of formula 2 are described by Derm et al in "Ethyleneimine and Other Aziridines" Academic Press, N.Y., 1969. A general review of methods of synthesis of intermediates of formula 2 is given by Michael Ellis Perlman, an inventor herein, in a State University of N.Y. thesis entitled "Synthesis and Mechanistic Studies Of Phosphoraziridines as Radiation Sensitizers" which was first published in July of 1982.

As previously discussed, the method of the invention comprises the chemical inhibition of the replication of tumor cells. In accordance with the method, a host organism containing tumor cells is administered an effective cell replication inhibiting concentration of a compound having a pH of 5 or above of the formula:

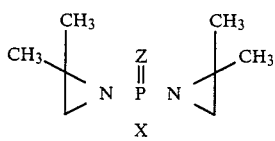

wherein X is selected from the group consisting of

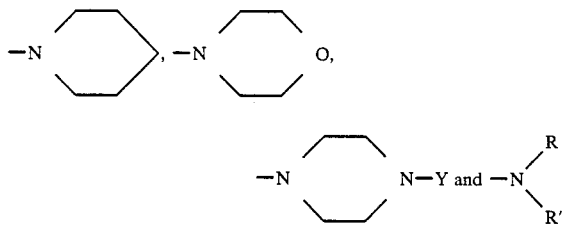

R and R' are each independently hydrogen, alkyl of 1 to 6 carbon atoms, substituted alkyl of 1 to 10 carbon atoms, phenyl and substituted phenyl; Y is alkyl or substituted alkyl of 1 to 10 carbon atoms and Z is oxygen or sulfur.

The effective cell replication inhibiting concentration of the compound of the invention usually ranges between about 0.5 and 1500 milligrams per kilogram of body weight and is preferably between about 1 and about 300 milligrams per kilogram of body weight of the host organism being treated. Though the most common method of treatment is by injection into the circulatory system of the host organism, other typical methods of the prior art are contemplated by the invention. After injection of the compound of the invention, sufficient time is permitted to allow the compound of the invention to collect at the tumor site.

The organisms which are treated in accordance with the method of the invention are usually mammals including human beings.

In accordance with the method of the invention, the growth of tumor cells can be chemically inhibited, with particular selectivity toward hypoxic (anaerobic) cells which is desirable since many tumors are hypoxic. A more effective and selective toxicity to tumor cells (cytotoxic) may therefore be realized, possibly with lower doses of the chemotherapeutic agent and with the likelihood of more specific localized toxic effect at the tumor site so that decreased incidence of toxic side effects to the overall organism may be achieved.

The following examples are meant to illustrate the invention and are not to be viewed as a limitation thereof. All temperatures are in degrees centigrade unless otherwise denoted and standard laboratory precautions were taken to avoid contamination by moisture.

EXAMPLE 1

Preparation of P,P-bis(2,2-dimethyl-1-aziridinyl)phosphinoyl chloride 0.08 moles of triethylamine, 0.025 moles of $POCl_3$ and 150 milliliter of dried tetrahydrofuran(THF) were combined in a 250 milliliter round bottom flask, under nitrogen atmosphere to avoid moisture contamination, to form a first solution which was then cooled to −40° C. A second solution was prepared containing 0.05 moles of 2,2-dimethylaziridine in 20 milliliters of THF and the second solution was added dropwise to the cooled first solution over a period of about 2 hours. The resulting slurry was then warmed to room temperature, over a 1 hour period, and then filtered under a nitrogen atmosphere to remove precipitated triethylamine hydrochloride. The remaining filtrate comprised 0.025 moles of P,P-bis(2,2-dimethyl-1-aziridinyl)phosphinoyl chloride and about 170 milliliters of THF.

In a similar manner, 0.08 moles of triethylamine, 0.025 moles of $PSBr_3$ and 150 milliliters of THF are combined and treated, by dropwise addition, with a solution containing 0.05 moles of 2,2-dimethylaziridine and 20 milliliters of THF. The resulting slurry is filtered to remove precipitated triethylamine hydrobromide and the filtrate is found to comprise about 0.025 moles of P,P-bis(2,2-dimethyl-1-aziridinyl)thiophosphinic bromide.

EXAMPLE 2

Preparation of P,P-bis(2,2-dimethyl-1-aziridinyl)phosphinic amide

A solution comprising 0.02 moles of P,P-bis(2,2-dimethyl-1-aziridinyl)phosphinoyl chloride and about 170 milliliters of THF, prepared in accordance with Example 1, was placed in a dry vessel fitted with a bubbler tube for the introduction of gaseous material below the liquid surface. The vessel and contents were cooled to about −10° C. and gaseous ammonia was bubbled into the solution until the solution appeared saturated therewith (about 1 hour). The thus saturated solution was allowed to sit overnight at 4° C. without stirring. The resulting product was filtered, washed and the filtrate was concentrated by rotary evaporation at room temperature. The thus concentrated filtrate was recrystallized from THF providing a 65% yield of P,P-(2,2-dimethyl-1-aziridinyl)phosphinic amide which was characterized by NMR and IR as having a purity of 99%. Elemental Analysis confirmed the structure contained the following:

| Found | Calculated |
|---|---|
| C-47.19% | 47.28% |
| H-8.95% | 8.93% |
| N-20.69% | 20.67% |

In a similar manner 0.025 moles of P,P-bis(2,2-dimethyl-1-aziridinyl)thiophosphinic bromide, and about 170 milliliters of THF, is saturated with gaseous ammonia at about −10° C. and the saturated solution is allowed to sit overnight without stirring. Upon filtration, concentration by rotary evaporation, and recrystallization, P,P-bis(2,2-dimethyl-1-aziridinyl)thiophosphinic amide is recovered at a purity in excess of about 95%.

EXAMPLE 3

Preparation of P,P-bis(2,2-dimethyl-1-aziridinyl)-N-methylphosphinic amide

A solution comprising 0.025 moles of P,P-bis(2,2-dimethyl-1-aziridinyl)phosphinoyl chloride in about 170 milliliters of THF, prepared in accordance with Example 1, was cooled to −15° C. and a saturated excess of gaseous methylamine was introduced to the solution through a bubbler tube in accord with the process of Example 2. The vessel and contents were warmed to about 4° C. and the saturated solution was allowed to sit overnight without stirring at that temperature. The resulting slurry was filtered and the filtrate was concentrated by rotary evaporation at room temperature. The thus concentrated filtrate was vacuum distilled at 94° C. and 0.14 millimeters of mercury providing a 75% yield of P,P-bis(2,2-dimethyl-1-aziridinyl)-N-methylphosphinic amide. NMR and aziridinyl titration characterization of the product indicated a purity of 98.4%.

In a similar manner 0.025 moles of P,P-bis(2,2-dimethyl-1-aziridinyl)thiophosphinic bromide in about 170 milliliters of THF, prepared in accordance with Example 1, is saturated with an excess of gaseous methylamine, kept overnight at 4° C., filtered, concentrated on a rotary evaporator at room temperature, and vacuum distilled to provide about 65% yield of P,P-bis(2,2-dimethyl-1-aziridinyl)-N methylthiophosphinic amide.

EXAMPLE 4

Preparation of P,P-bis(2,2-dimethyl-1-aziridinyl)-N,N-dimethylphosphinic amide 0.16 moles of triethylamine, 0.05 moles of $POCl_3$ and 150 milliliters of dried tetrahydrofuran were combined in a 250 milliliter round bottom flask, under a nitrogen atmosphere to avoid moisture contamination, to form a first solution which was then cooled to −40° C. A second solution was then prepared containing 0.10 moles of 2,2-dimethylaziridine in 20 milliliters of THF and the second solution was added dropwise to the cooled first addition over a period of about 2 hours. The resulting slurry was then warmed to approximately 0° C. over an hours' time and thereafter cooled again to −20° C. A third solution was then prepared containing 0.16 moles of dimethylamine in 25 milliliters of dried THF and the third solution was added dropwise to the cooled aforesaid combination of the first and second solutions over a period of about 2 hours. The vessel was sealed and stirred overnight at 4° C. The resulting slurry was then filtered, the filtrate was concentrated by rotary evaporation, and thereafter vacuum distilled at 58° C./0.15 millimeters Hg to produce at 75% yield of P,P-bis(2,2-dimethyl-1-aziridinyl)-N,N-dimethylphosphinic amide. The product was characterized by NMR and aziridine titration as having a purity of 99.45%. Elemental analysis confirmed the structure as follows:

| Found | Calculated |
|---|---|
| % C = 51.96 | 51.97 |
| % H = 9.60 | 9.59 |
| % N = 18.14 | 18.17 |

In a similar manner 0.16 moles of triethylamine, 0.05 moles of $PSBr_3$ and 150 milliliters of dried tetrahydrofuran are combined in a 250 milliliter round bottom flask which is thereafter treated with a first solution containing 0.10 moles of 2,2-dimethylaziridine in 20 milliliters of THF and a second solution containing 0.16 moles of dimethylamine in 25 millimeters of dried THF, to produce a slurry which after filtration, concentration of the filtrate and vacuum distillation affords about 65% yield of P,P-bis(2,2-dimethyl-1-aziridinyl)-N-N-dimethylthiophosphinic amide.

EXAMPLE 5

Preparation of P,P-bis(2,2-dimethyl-1-aziridinyl)-N-(3-methoxy-1-propyl)phosphinic amide 0.08 moles of triethylamine, 0.025 moles of $POCl_3$ and 150 milliliters of dried tetrahydrofuran were combined in a 250 milliliter round bottom flask, under a nitrogen atmosphere to avoid moisture contamination, to form a first solution which was then cooled to −40° C. A second solution was then prepared containing 0.05 moles of 2,2-dimethylaziridine in 20 milliliters of THF and the second solution was added dropwise to the cooled first solution over a period of about 2 hours. The resulting slurry was then warmed over a period of about 1 hour to 0° C. then cooled again to −30° C. and then had added thereto, by dropwise addition, a solution containing 0.026 moles of 3-methoxypropyl amine in 20 milliliters of THF. The solution was then allowed to stand overnight with constant stirring at ambient temperature, the resulting slurry was filtered, the filtrate was concentrated by rotary evaporation, and thereafter vacuum distilled at 130° C./0.42 millimeters Hg to produce a 60% yield of 3-methoxypropylamino phosphoraziridine. NMR characterization indicated that the product was 95% pure.

EXAMPLE 6

Preparation of P,P-bis(2,2-dimethyl-1-aziridinyl)-N-(3-dimethylaminopropyl)phosphinic amide A solution containing 0.025 moles of P,P-bis(2,2-dimethyl-1-aziridinyl)phosphinyl chloride in about 170 milliliters of THF was prepared in accordance with Example 1, chilled to −40° C. and treated, by slow dropwise addition, with a solution containing 0.026 moles of 3-dimethylaminopropylamine, in 25 milliliters of THF. The resulting slurry was stirred overnight at ambient temperature, filtered, the filtrate was concentrated by rotary evaporation, and vacuum distilled at 119° C./0.45 millimeter of mercury to produce a 40% yield of P,P-bis(2,2-dimethyl-1-aziridinyl)-N-(3-dimethylaminopropyl)phosphinic amide. NMR characterization confirmed the product was 99% pure. Elemental analysis confirmed the structure contained the following:

| Found | Calculated |
|---|---|
| % C = 53.89 | 54.14 |
| % H = 10.17 | 10.14 |
| % N = 19.38 | 19.43 |

In a similar manner 0.025 moles of P,P-bis(2,2-dimethyl-1-aziridinyl)thiophosphinic bromide and about 170ml of THF are treated by dropwise addition with 0.02 moles of 3-dimethylaminopropyl amine in 25 millimeters of THF stirred for several hours at ambient temperature, filtered, concentrated by rotary evaporation, and vacuum distilled to produce about 35% yield of P,P-bis(2,2-dimethyl-1-aziridinyl)-N-(3-dimethylaminopropyl)thiophosphinic amide.

In a similar manner 0.025 moles of P,P-bis(2,2-dimethyl-1-aziridinyl)phosphinoyl chloride in about 170 mL of THF are treated by dropwise addition with 0.026 moles of 5-diethylaminopentylamine in 25 mL of THF, stirred for several hours at ambient temperature, filtered, concentrated by rotary evaporation and vacuum distilled to yield about 90% pure P,P-bis(2,2-dimethyl-1-aziridinyl)-N-(5-diethylamino-1-pentyl)-phosphinic amide.

EXAMPLE 7

Preparation of P,P-bis(2,2-dimethyl-1-aziridinyl)phosphoric anilide 0.025 moles of $POCl_3$ and 0.079 moles of triethylamine was combined with 150 milliliters of THF, cooled to $-40°$ C. and added over a 1 hour period, by dropwise addition, to a solution containing 20 milliliters of THF and 0.025 moles of aniline. The slurry was allowed to warm slowly to 10° C., over a 1 hour period and is then treated, by dropwise addition, with a solution containing 0.05 moles of 2,2-dimethylaziridine in 20 milliliters of THF. The slurry was allowed to warm to ambient temperature and was stirred overnight at this temperature. The slurry was filtered, the filtrate was concentrated at room temperature by rotary evaporation, resulting in a fine white powder in residual oils. The mixture of powder and residual oils was washed with a 10 milliliter quantity of dry ethyl ether, filtered to remove the solid product, and resulted in a 20% yield of the desired P,P-bis(2,2-dimethyl-1-aziridinyl)phosphinic anilide, which was characterized by NMR, as 99% pure.

EXAMPLE 8

Preparation of P,P-bis(2,2-dimethyl-1-aziridinyl phosphinic piperidide

A. To a well stirred solution of 1.0 equivalent of $POCl_3$ and a 5–10% excess over 3.0 equivalents of triethylamine in THF chilled to $-40°$ C. under $N_2$, is slowly added, by way of a dropping funnel, a solution of 2.0 equivalents of 2,2-dimethylaziridine in THF, over a period of 1–2 hours. The resulting product comprises a THF solution of P,P-bis(2,2-dimethyl-1-aziridinyl)phosphinic chloride.

B. The unfiltered above product was chilled to $-30°$ C. and to it was slowly added 1.05–1.2 equivalents of piperidine in 20 mL of THF at a moderate rate from a dropping funnel. The mixture was stirred overnight, at 4° C. and subsequently filtered to remove amine hydrochloride. The resulting filtrate was vacuum distilled to provide a 51.6% yield of impure product. The impure product was purified by silica gel chromatography using a 50:50 acetone/$CH_2Cl_2$ with 1% added triethylamine to provide a 37.2% yield of the purified slightly yellow oil, pure desired product.

EXAMPLE 9

Preparation of P,P-bis(2,2-dimethyl-1-aziridinyl)phosphinic morpholide

Using the same procedure as Example 8 with the exception that morpholine was used as a reactant instead of piperidine a 72.8% yield of impure product was recovered. The impure product was filtered through a 5 cm bed of silica gel with THF as eluent, under pressure and redistillation of the eluate, bulb to bulb under vacuum, gave a 94% recovery of the oil, pure, desired product.

EXAMPLE 10

Preparation of P,P-bis(2,2-dimethyl-1-aziridinyl)phosphinic N'-methyl piperazide Using the same procedure on Example 8, with the exception that N-methyl piperazine was the reactant instead of piperidine an impure product was recovered. The product was filtered through a 4 cm bed of silica gel with THF eluent to remove impurities and the reconcentrated eluent was then vacuum distilled bulb to bulb to give a 67.4% yield of the colorless oil, pure, desired product.

EXAMPLE 11

Preparation of P,P-bis(2,2-dimethyl-1-aziridinyl)phosphinic N-cyclohexylamide (14)

A solution of cyclohexylamine (2.10 g, 0.021 mole) in 5 mL of dry diethyl ether was added over 20 min by dropping funnel to $POCl_3$ (1.53 g, 0.01 mole) in 20 mL dry ether at 2° C. under $N_2$. The resulting slurry was stirred for 1 hour at 0° C. and for 3 hour at ambient temperature, then was filtered to remove the cyclohexylammonium chloride byproduct. The dichloridate solution was transferred to a dropping funnel and added over 30 min to a solution of 2,2-dimethylaziridine (1.49 g, 0.021 mole) and triethylamine (2.13 g, 0.021 mole) in 25 mL of ether at 0°–2° C. under $N_2$. Stirring was continued at 4° C. overnight, then the suspension was filtered and the filtrate concentrated at reduced pressure. Recrystallization (twice) from ethyl ether yielded 0.793 g (27.8%) of colorless crystals: mp 110°–112° C., being confirmed by TLC to be the desired product.

EXAMPLE 12

Various bis(2,2-dimethyl-1-aziridinyl)phosphinic amides, prepared in accord with Examples 1–11 and designated Samples A–M, were tested for antitumor activity in vivo using the lymphocytic leukemia P-388 in mice. The test system was that employed by the National Cancer Institute (NCI) for the primary screening of antitumor agents, according to Protocol 1.200 (Cancer Chemo. Rpts. Part 3, Vol. 3, No. 2, P. 9; 1972). In the study $10^6$ ascites cells were implanted in the peritoneal cavity of $CDF_1$ female mice. Each amide was given in a single injection, at six or four dose levels (6 mice/dose level). The control animals received saline (10 mice). Test criteria was in accord with NCI protocol as follows: toxicity is indicated where <4/6 or <¾ mice are alive on Day 5; antitumor activity is indicated when % T/C>125 [%T/C=(MST treated/MST control) X 100, where MST=medium survival time]. The results are shown in Table I.

EXAMPLE 13

Samples A–K were tested for antitumor activity in vivo using B16 Melanoma in mice. $BDF_1$ mice were implanted with tumor fragments subcutaneously (sc) or by intraperitoneal (ip) injection with 0.5 mL of 10% weight/volume tumor brei suspension. The results were recorded for optimal dosage (mg/kg) without excessive toxicity. Each amide was given to 10 mice per dose level and % T/C, as calculated in Example 12, for the optimal level was recorded. The results are shown in Table II.

EXAMPLE 14

Samples A, B and C were tested for L1210 leukemia activity using the method of Example 12 but with L1210 rather than P-388 leukemia. The results are shown in Table III.

EXAMPLE 15

M109 and C26 experiments were initiated by implanting $CDF_1$ mice with 0.3 mL intraperitoneal or 0.1 mL subcutaneously of 2% (M109) or 1% (C26) tumor brei suspension. 8 mice were used for each sample per dose level. The results were recorded for optimal dosage (mg/kg) without excessive toxicity. The results are tabulated in Table IV.

TABLE I
Anti-tumor Activity on P388 Leukemia (% T/C)

| Sample | Compound | 256 | 128 | 64 | 32 | 16 | 8 |
|---|---|---|---|---|---|---|---|
| A | bis(2,2-dimethyl-1-aziridinyl) phosphinic amide | 206 | 188 | 159 | 153 | 147 | 124 |
| B | bis(2,2-dimethyl-1-aziridinyl) N—methyl-phosphinic amide | toxic | 239 (1)* | 211 | 206 | 167 | 144 |
| C | bis(2,2-dimethyl-1-aziridinyl) N,N—dimethyl-phosphinic amide | toxic (1)* | 272 | 217 | 183 | 150 | 133 |
| D | bis(2,2-dimethyl-1-aziridinyl) -N—ethyl-phosphinic amide | 288 | 225 | 206 | 188 | | |
| E | bis(2,2-dimethyl-1-aziridinyl) -N—propylphosphinic amide | >363 (3)* | 231 (1)* | 194 | 194 | | |
| F | bis(2,2-dimethyl-1-aziridinyl) -N—butylphosphinic amide | 238 | 200 | 188 | 175 | | |
| G | bis(2,2-dimethyl-1-aziridinyl) -N',N'—dimethyl-N—aminopropyl phosphinic amide | toxic (1)* | toxic (1)* | 231 | 213 | | |
| H | bis(2,2-dimethyl-1-aziridinyl) -N—methoxypropyl phosphinic amide | 225 (1)* | 219 (1)* | 195 | 175 | | |
| I | P,P—bis(2,2-dimethyl-1-aziridinyl) phosphinic piperidide | 218 | 176 | 176 | 153 | 147 | 124 |
| J | P,P—bis(2,2-dimethyl-1-aziridinyl) phosphinic morpholide | 247 | 200 | 182 | 159 | 147 | 135 |
| K | P,P—bis(2,2-dimethyl-1-aziridinyl) phosphinic-N'—methyl piperazide | — | 224 | 176 | 165 | 165 | 147 |
| L | P,P—bis(2,2-dimethyl-1-aziridinyl) phosphinic-N—cyclohexylamide | 106 | | | | | |
| M | bis(2,2-dimethyl-1-aziridinyl) -N—phenyl-phosphinic amide | 169 | 128 | 144 | 144 | | |

( )*-30 Day Survivors

TABLE II
Effect of Selected Phosphoraziridines on B16 Melanoma

| Sample | Opt. Dose (mg/kg/inj.)[a] | Max. % T/C (cures/total)[b] |
|---|---|---|
| A | 100 | 310(3/10) |
| A | 100 | 181 |
| A | 40 | 214(2/10) |
| A | 120[c] | 191 |
| A | 120 | 180 |
| A | 80 | 210 |
| B | 60 | 120 |
| B | 120[c] | 153 |
| C | 60 | 118 |
| C | 120[c] | 153 |
| D | 120[c] | 148 |
| E | 80 | 162 |
| E | 120 | 144 |
| F | 120[c] | 157 |
| G | 80[c] | 210(2/10) |
| G | 80 | 172 |
| H | 80 | 160 |
| I | 160[c] | 132 |
| J | 160[c] | 160 |
| K | 80 | 170 |

[a]Administered ip on Days 1, 5, and 9 following ip implant of 0.5 mL of 10% w/v tumor breis. Optimal dose is that dosage which gives the maxial therapeutic effect without unacceptable toxicity (or the arbitrarily chosen maximum dosage, (if indicated).
[b]T/C is a ratio of average life span of the 10 treated mice to that of the 10 untreated control mice. "Cures" were tumor-free mice surviving to Day 60.
[c]Highest dose-level evaluated

TABLE III
Effect of Three New Phosphoraziridines on L1210 Leukemia

| Sample | Opt. Dose (mg/kg)[a] | Max. % T/C |
|---|---|---|
| A | 60[b] | 164 |
| B | 180[c] | 207 |
| C | 180[c] | 207 |

[a]Administered ip on Day 1 following ip implant of $10^6$ L1210 cells, in 6 mice per dosage tested.
[b]At a higher dose of 180 mg/kg, compound 3 caused a T/C of 357% including two of six mice cured. But this result was achieved at the cost of two of six early deaths which was judged to be unacceptable toxicity.
[c]Highest dose level evaluated.

TABLE IV
Advanced Antitumor Testing of Selected Phosphoraziridines

| Tumor, Implant Site[a] | Sample | Opt. Dose (mg/kg/inj) | Treatment Schedule | route | Max. % T/C (cures/total)[b] |
|---|---|---|---|---|---|
| C26 ip | A | 120 | d.1,4 | ip | 190(3/8) |
|  | A | 80 | d.1,4 | ip | 221(2/8) |
|  | B | 60 | d.1,4 | ip | 166 |
|  | C | 80 | d.1,4 | ip | 127 |
|  | G | 50 | d.1,4 | ip | 170 |
| C26 sc | A | 50 | d.1,4 | ip | 127 |
|  | B | 25 | d.1,4 | ip | 151 |
|  | C | 60 | d.1,4 | ip | 125 |
| M109 ip | A | 150 | d.1,4 | ip | 157 |
| M109 | A | 70 | d.1,4 | ip | 99 |

TABLE IV-continued

| Tumor, Implant Site[a] | Sample | Opt. Dose (mg/kg/inj) | Treatment Schedule, route | Max. % T/C (cures/total)[b] |
|---|---|---|---|---|
| sc | A | 70 | d.1,4  iv[c] | 104 |

[a]Tumor implant levels are described in the Materials and Methods section.
[b]"Cures" were tumor-free mice surviving to Day 60 or beyond.
[c]Intravenous

What is claimed is:

1. A method for inhibiting the replication of solid skin cancer tumor cells which comprises administering to said tumor cells an effective tumor cell inhibiting concentration of a compound of the formula:

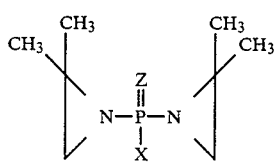

wherein X is

wherein R and R' are independently hydrogen, alkyl of 1–6 carbon atoms, substituted alkyl of 1–10 carbon atoms, phenyl or substituted phenyl, Y is alkyl or substituted alkyl of 1–10 carbon atoms wherein the substituents on the substituted moieties are selected from halogen, hydroxy, lower alkoxy, nitro, amine and sulfonate, and, Z is oxygen or sulfur.

2. The method of claim 1 wherein said tumor is in a mammal.

3. The method of claim 2 comprising injecting said mammal with an amount of said compound which is from about 0.5 to about 1500 milligrams per kilogram of body weight of the mammal.

4. The method of claim 2 wherein the compound is P,P-bis(2,2-dimethyl-1-aziridinyl)-N-(3-methoxy-1-propyl)phosphinic amide.

5. The method of claim 2 wherein the compound is P,P-bis(2,2-dimethyl-1-aziridinyl)-N-(3-dimethylaminopropyl)phosphinic amide.

6. The method of claim 2 wherein the compound is P,P-bis(2,2-dimethyl-1-aziridinyl)-N-butylphosphinic amide.

7. The method of claim 2 wherein the compound is P,P-bis(2,2-dimethyl-1-aziridinyl)phosphinic amide.

8. The method of claim 2 wherein the compound is P,P-bis(2,2-dimethyl-1-aziridinyl)-N-methylphosphinic amide.

9. The method of claim 2 wherein the compound is P,P-bis(2,2-dimethyl-1-aziridinyl)-N-N-dimethylphosphinic amide.

10. The method of claim 2 wherein the compound is P,P-bis(2,2-dimethyl-1-aziridinyl)-N-ethylphosphinic amide.

11. The method of claim 2 wherein the compound is P,P-bis(2,2-dimethyl-1-aziridinyl)-N-propylphosphinic amide.

12. The method of claim 2 wherein the compound is P,P-bis(2,2-dimethyl-1-aziridinyl)-N',N'-diethylamino-1-pentyl phosphinic amide.

13. The method of claim 2 wherein the compound is P,P-bis(2,2-dimethyl-1-aziridinyl)-N-phenyl-phosphinic amide.

14. The method of claim 2 wherein the compound is P,P-bis(2,2-dimethyl-1-aziridinyl)-N-cyclohexylphosphinic amide.

15. The method of claim 3 wherein the compound is injected intravenously.

16. The method of claim 3 wherein the amount is from about 1 to about 300 milligrams per kilogram of body weight.

17. The method of claim 3 wherein the compound is injected intraperitoneally, orally or intramuscularly.

18. A method for inhibiting the replication of solid skin cancer tumor cells which comprises administering to said tumor cells an effective tumor cell inhibiting concentration of a compound selected from the group consisting of: P,P-bis(2,2-dimethyl-1-asiridinyl)-N-(3-methoxy-1-propyl)phosphinic amide; P,P-bis(2,2-dimethyl-1-asiridinyl)-N-(3-dimethylaminopropyl)-phosphinic amide; P,P-bis(2,2-dimethyl-1-aziridinyl)-N-butylphosphinic amide; P,P-bis(2,2-dimethyl-1-aziridinyl)phosphinic amide; P,P-bis(2,2-dimethyl-1-aziridinyl)-N-methylphosphinic amide; P,P-bis(2,2-dimethyl-1-aziridinyl-N-N-dimethylphosphinic amide; P,P-bis(2,2-dimethyl-1-aziridinyl)-N-ethylphosphinic amide; P,P-bis(2,2-dimethyl-1-aziridinyl)-N-propyl-phosphinic amide; P,P-bis(2,2-dimethyl-1-aziridinyl)-N',N'-diethylamino-1-pentyl phosphinic amide; P,P-bis(2,2-dimethyl-1-aziridinyl)-N-phenyl-phosphinic amide; and P,P-bis(2,2-dimethyl-1-aziridinyl)-N-cyclohexylphosphinic amide.

* * * * *

UNITED STATES PATENT AND TRADEMARK OFFICE
CERTIFICATE OF CORRECTION

PATENT NO. : 4,886,790
DATED : December 12, 1989
INVENTOR(S) : Thomas J. Bardos et al.

It is certified that error appears in the above-identified patent and that said Letters Patent is hereby corrected as shown below:

Title Page:
In the ABSTRACT, line 4 should read:

wherein X is $-N{<}^R_R$, lines 6 and 7 of the ABSTRACT, the following should be deleted:

"...,Y is alkyl or substituted alkyl of 1-10 carbon atoms ..."

Column 15, lines 35 and 36 (Claim 1), of the following should be deleted:

"...,Y is alkyl or substituted alkyl of 1-10 carbon atoms ..."

Signed and Sealed this

Fifth Day of February, 1991

Attest:

HARRY F. MANBECK, JR.

Attesting Officer    Commissioner of Patents and Trademarks